United States Patent

Rossi et al.

Patent Number: 5,202,325
Date of Patent: Apr. 13, 1993

[54] USE OF ERGOLINE DERIVATIVES IN TREATING EMESIS

[75] Inventors: Alessandro Rossi; Metilde Buonamici, both of Parabiago; Lorenzo Pegrassi, Milan; Enzo Brambilla, Mariano Comense, all of Italy

[73] Assignee: Farmitalia Carlo Erba S r L, Milan, Italy

[21] Appl. No.: 499,413

[22] PCT Filed: Oct. 20, 1989

[86] PCT No.: PCT/EP89/01263
    § 371 Date: Jul. 12, 1990
    § 102(e) Date: Jul. 12, 1990

[87] PCT Pub. No.: WO90/04396
    PCT Pub. Date: May 3, 1990

[30] Foreign Application Priority Data

Oct. 21, 1988 [GB] United Kingdom ............ 8824744

[51] Int. Cl.⁵ ................. A01N 43/60; A01N 43/42
[52] U.S. Cl. ................... 514/255; 514/288; 514/872
[58] Field of Search ........... 514/284, 288, 255, 872

[56] References Cited

U.S. PATENT DOCUMENTS 4,853,390 8/1989 Hilsher ............... 514/288
4,950,672 8/1990 Haefliger ............. 514/288

FOREIGN PATENT DOCUMENTS 0197241 10/1986 European Pat. Off.
0218433 4/1987 European Pat. Off.
0219257 4/1987 European Pat. Off.
2710246 9/1977 Fed. Rep. of Germany.

OTHER PUBLICATIONS

Goodman & Gilman "*The Pharmacological Basis...*" p. 259 (1985).

Primary Examiner—Frederick E. Waddell
Assistant Examiner—Gregory Hook
Attorney, Agent, or Firm—Oblon, Spivak, McClelland, Maier & Neustadt

[57] ABSTRACT

Compounds of the formula I

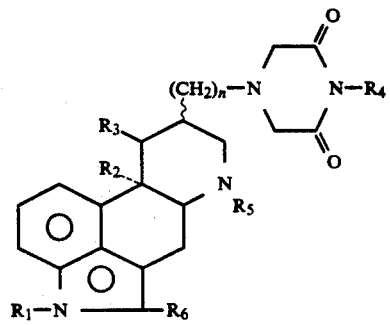

wherein n is 1 or 2, $R_1$ represents a hydrogen atom or a $C_1$-$C_4$ alkyl group, $R_2$ represents a hydrogen atom and $R_3$ represents a hydrogen atom or a hydroxy group or $R_2$ and $R_3$ together represent a chemical bond, $R_4$ represents a hydrogen atom, or a phenyl or $C_1$-$C_4$ alkyl group, $R_5$ represents a $C_1$-$C_4$ alkyl group or an alkyl group and $R_6$ represents a hydrogen or halogen atom, and the pharmaceutically acceptable salt thereof, are useful for the manufacture of a pharmaceutical composition useful in the treatment of emesis.

8 Claims, No Drawings

USE OF ERGOLINE DERIVATIVES IN TREATING EMESIS

The present invention relates to a new therapeutic use of ergoline derivatives having the formula I

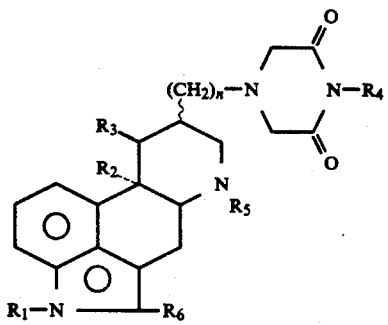

wherein n is 1 or 2, $R_1$ represents a hydrogen atom or a $C_1$–$C_4$ alkyl group, $R_2$ represents a hydrogen atom and $R_3$ represents a hydrogen atom or a hydroxy group or $R_2$ and $R_3$ together represent a chemical bond, $R_4$ represents a hydrogen atom or a phenyl or $C_1$–$C_4$ alkyl group, $R_3$ represents a $C_1$–$C_4$ alkyl group or an allyl group and $R_6$ represents a hydrogen or halogen atom; and the pharmaceutically acceptable salts thereof.

The compounds of the formula I and their preparation are described in EP-A-0197241 or can be prepared by techniques analogous to those described in EP-A-0197241. EP-A-0197241 shows the functional anti-dopaminergic activity of certain ergoline derivatives in normal mice. The compounds are said to have moderate to good anti-hypertensive activity and to be useful as anxiolytic and antipsychotic agents.

It has been found that the ergoline derivatives of the formula I may be unexpectedly used in the treatment of other diseases different from psychosis and anxiety. The compounds of formula (I) block the emetic response induced by cytotoxic agents such as cisplatin and also by radiation treatment. The compounds are therefore of use in the treatment of nausea and vomiting associated with cancer therapy.

Accordingly, the present invention provides the use of a compound of the formula (I) or a pharmaceutically acceptable salt thereof in the preparation of a pharmaceutical composition for treating emesis. The pharmaceutical composition containing the compound of formula I or salt thereof as active agent can therefore be prepared by a process characterised in that the active agent, which has been prepared in a known way, is admixed with a pharmaceutically acceptable carrier and/or diluent and then transformed into a pharmaceutical preparation suitable for treating emesis.

The invention further provides:
- an agent for use in treating emesis, comprising a compound of formula I or a pharmaceutically acceptable salt thereof; and
- a method of treating emesis, which method comprises administering to a patient in need of said treatment a therapeutically effective amount of a compound of formula I or a pharmaceutically acceptable salt thereof.

In formula (I), a $C_1$–$C_4$ alkyl group may be a methyl, ethyl, n-propyl, iso-propyl, n-butyl, iso-butyl or t-butyl group. $R_1$ is generally a hydrogen atom or a methyl or iso-propyl group, preferably a hydrogen atom or a methyl group.

$R_4$ is preferably methyl or hydrogen. $R_5$ may be methyl, ethyl, n-propyl, iso-propyl, n-butyl, sec-butyl, t-butyl, iso-butyl or allyl. Preferably $R_5$ is methyl. When $R_6$ is halogen, it may be fluorine, chlorine or bromine. Preferably $R_6$ is chlorine or bromine or hydrogen.

The wavy lines (∼) in formula I indicate that the substituents in the 8- or 9-position may be either in the α-configuration, i.e. below the plane of the ring, or in the β-configuration, i.e. above the plane of the ring, or in both, i.e. a mixture thereof such as a diasteroisomer. Preferably the substituent in the 8-position is in the β-configuration and the substituent in 9-position is in the α-configuration.

Preferred ergoline derivatives for use in the present invention are identified in Table I.

TABLE I

| Laboratory Code | Chemical Name | Reference |
|---|---|---|
| FCE 23884 | 6-Methyl-9,10-didehydro-8β-(3,5-dioxo-piperazin-1-yl-methyl)-ergoline (I: $R_1 = R_4 = R_6 = H$, $R_5 = CH_3$ $R_2 + R_3 =$ bond, n = 1) | EP-A-197241 Example 5 |
| FCE 23952 | 1,5-Dimethyl-8β-(3,5-dioxo-piperazin-1-yl-methyl)-ergoline (I: $R_2 = R_3 = R_4 = R_6 = H$, $R_1 = R_5 = CH_3$, n = 1) | EP-A-197241 Example 2 |
| FCE 23710 | 6-Methyl-8β-(3,5-dioxo-4-methyl-piperazin-1-yl-methyl)-ergoline (I: $R_1 = R_2 = R_3 = R_6 = H$, $R_4 = R_5 = CH_3$, n = 1) | EP-A-197241 Example 3 |
| FCE 23308 | 6-Methyl-8β-(3,5-dioxo-piperazin-1-yl-methyl)-ergoline(I: $R_1 = R_2 = R_3 = R_4 = R_6 = H$, $R_5 = CH_3$, n = 1) | EP-A-197241 Example 1 |

The following compounds were prepared analogously to those specifically described in EP-A-197241:

6-Methyl-9,10-didehydro-8α-(3,5-dioxopiperazin-1-yl-methyl)-ergoline (I:$R_1=R_4=R_6=H$, $R_5=CH_3$, $R_2+R_3=$bond, n=1)

6-Allyl-9,10-didehydro-8β-(3,5-dioxopiperazin-1-yl-methyl)-ergoline (I:$R_1=R_4=R_6=H$, $R_5=$allyl, $R_2+R_3=$bond, n=1)

6-Propyl-9,10-didehydro-8α-(3,5-dioxopiperazin-1-yl-methyl) ergoline (I:$R_1=R_4=R_6=H$, $R_5=$propyl, $R_2+R_3=$bond, n=1)

2-Chloro-6-methyl-9,10-didehydro-8β-(3,5-dioxopiperazin-1 yl-methyl)-ergoline (I:$R_1=R_4=H$, $R_5=CH_3$, $R_6=Cl$, $R_2+R_3=$bond, n=1)

2-Bromo-6-methyl-9,10-didehydro-8β-(3,5-dioxopiperazin-1 yl-methyl)-ergoline (I:$R_1=R_4=H$, $R_5=CH_3$, $R_6=Br$, $R_2+R_3=$bond, n=1), m.p. 242°–245° C.

1,6-Dimethyl-9,10-didehydro-8β-(3,5-dioxo-piperazin-1-yl-methyl)-ergoline (I:$R_1=R_5=CH_3$, $R_4=R_6=H$, $R_2+R_3=$bond, n=1), m.p. 216°–218° C.

6-Methyl-9,10-didehydro-8β-(3,5-dioxo-piperazin-1-ethyl)-ergoline (I:$R_1=R_4=R_6=H$, $R_5=CH_3$, $R_2+R_3=$bond, n=2), m.p. 242°–244° C.

6-Methyl-9α-hydroxy-8β-(3,5-dioxo-piperazin-1-ylmethyl)ergoline (I:$R_1=R_2=R_4=R_6=H$, $R_5=CH_3$, $R_3=OH$, n=1), m.p. 278°–280° C.

6-Methyl-9,10-didehydro-8β-(3,5-dioxo-4-phenyl-piperazin-1 -ylmethyl)-ergoline (I:$R_1=R_6=H$, $R_5=CH_3$, $R_2+R_3=$bond, $R_4=$phenyl, n=1) m.p. 240°–242° C.

6-Methyl-9,10-didehydro-8β-(3,5-dioxo-4-methyl-piperazin-16 1-ylmethyl)-ergoline (I:$R_1=R_6=H$, $R_4=R_5=CH_3$, $R_2+R_3$=bond, n=1) m.p. 227°-229° C.

1-Methylethyl-6-methyl-9,10-didehydro-8β-(3,5-dioxopiperazin-1-yl-methyl)-ergoline (I: $R_4=R_6=H$, $R_1=i-C_3H_7$, $R_5=CH_3$, $R_2+R_3$=bond, n=1), m.p. 137°-140° C.

6-Propyl-9,10-didehydro-8β-(3,5-dioxo-piperazin-1-yl methyl)-ergoline (I: $R_1=R_4=R_6=H$, $R_5=n-C_3H_7$, $R_2+R_3$=bond, n=1), m.p. 250°-253° C.

1-Ethyl-6-methyl-9,10-didehydro-8β-(3,5-dioxo-piperazin-1-ylmethyl)-ergoline (I: $R_1=R_4=R_6=H$, $R_5=C_2H_5$, $R_2+R_3$=bond, n=1) m.p. 221°-223° C.

The ergoline derivatives of formula I and their pharmaceutically acceptable salts are useful in the treatment of emesis induced by cytotoxic agents. Thus, they may be used for the preparation of medicaments effective in the treatment of nausea and vomiting associated with cancer therapy.

Accordingly, the compounds of formula (I) and their pharmaceutically acceptable salts can be used to treat emesis induced by cytotoxic agents by administering to a patient in need of said treatment a therapeutically effective amount of a said compound or salt.

Examples of cytotoxic agents include those routinely used in cancer chemotherapy, such as cisplatin, doxorubicin, cyclophosphamide, particularly cisplatin. The administration of the compound of formula (I), or a pharmaceutically acceptable salt thereof may be by way of oral or parenteral administration.

An amount effective to treat the disorders hereinbefore described depends on the relative efficacies of the compounds of the invention, the nature and severity of the disorder being treated and the weight of the mammal. However, a unit dose for a 70 kg adult will normally contain 0.5 to 100 mg of the compound of formula (I), or a pharmaceutically acceptable salt thereof.

Unit doses may be administered once or more than once a day, for example, 2, 3 or 4 times a day, more usually 1 to 3 times a day, that is in the range of approximately 0.001 to 50 mg/kg/day, more usually 0.002 to 25 mg/kg/day. No adverse toxicological effects are indicated at any of the aforementioned dosage ranges.

ADMINISTRATION AND COMPOSITIONS

Administration of the active compound and salts described herein can be via any of the accepted modes of administration for antiemesis agents.

The routes for administration include parenteral, oral, buccal, peroral, transdermal, intranosal or other suitable routes. Orally administrable compositions are preferred, since they are more convenient for general use.

Depending on the intended route of administration, such compositions may be formulated in conventional manner or other pharmaceutical systems for delivery of the drug in a rate and extent needed for the intended therapeutical use. The composition will include a conventional pharmaceutical carrier or excipient and an active compound of formula (I) or the pharmaceutically acceptable salts thereof and, in addition, may include other medicinal agents, pharmaceutical agents, carriers, adjuvants, etc.

For solid compositions, conventional non toxic solid carriers including, for example, pharmaceutical grades of mannitol, lactose, starch, magnesium stearate, sodium saccharin, talcum, cellulose, glucose, sucrose, magnesium carbonate and the like may be used. Liquid pharmaceutically administerable compositions can, for example, be prepared by dissolving, dispersing, etc., an active compound as defined above and optional pharmaceutical adjuvant in a carrier such as, for example, water, saline, aqueous dextrose, glycerol, ethanol and the like, to thereby form a solution or suspension.

The following pharmacological data illustrate the invention.

PHARMACOLOGICAL DATA

Inhibition of Apomorphine and Chemotherapy—Induced Emesis

Male and female adult beagles (body weight 13-18 kg), bred at Morini Laboratories (CR, Italy), were individually housed and fed (300 g standard diet Altromin (Trade Mark)) two hours before the experiment with water ad libitum.

1) Inhibition of Apomorphine—Induced Emesis

Dogs were given a subcutaneous injection of 0.1 mg/kg apomorphine, which reliably induces emesis within 5-10 minutes in all tested animals.

Protection against apomorphine-induced emesis is a measure of the test compound's dopamine antagonism at the chemoreceptor trigger zone in the area postrema. FCE 23884 was given subcutaneously (s.c.) 30 min before the agonist. Number of emetic episodes and the latency of onset prior to the first expulsion of gastric content (latency time) were evaluated for each animal within two hours from administration of the agonist.

2) Inhibition of Cisplatin—Induced Emesis

FCE 23884 or the carrier or the reference compound (metoclopramide) were administered to dogs intravenously (i.v.) 30 min before and two hours after the intravenous injection of 3 mg/kg cisplatin. This dose of the chemotherapic agent induced emesis in 100% of treated animals.

The antiemetic effect was evaluated for five hours after the administration of the agonist.

The number of emetic episodes and the latency time for each dog were accounted for.

RESULTS

Inhibition of Apomorphine—Induced Emesis

FCE 23884, at the dose of 50 μg/kg s.c., completely prevented the apomorphine—induced emesis in all treated animals; at the dose of 10 μg/kg s.c., 2/6 animals were still completely protected from emesis; with this dosage, the remaining dogs showed an increased latency time and a lower number of emetic responses. At the lowest dose (5 μg/kg s.c.) the two-treated animals vomited but they still showed a lower number of emetic episodes (see Table II).

2) Inhibition of Cisplatin—Induced Emesis

FCE 23884, at the dose of 250 μg/kg i.v., completely antagonized cisplatin-induced emesis; at the dose of 125 μg/kg i.v., 3/4 dogs were still completely protected from emesis; the remaining animal showed only one emetic response with a delayed latency time. At the lowest dose, (62.5 μg/kg i.v.), 1/4 animal was still quite protected (see Table II). The reference compound, metoclopramide, displayed the expected antagonistic effect at the dose of 6 mg/kg i.v.; indeed 5/6 treated animals were completely protected from emesis.

CONCLUSIONS

Subcutaneous and intravenous FCE 23884 exhibited definite activity against respectively apomorphine and chemotherapy induced emesis in the dog. The compound was extremely active in antagonizing apomorphine-induced emesis: 50 μg/kg s.c. completely protected from emesis all the treated animals; intravenously administered, FCE 23884, at the dose of 125 μg/kg, almost completely inhibited the emetic responses following the administration of the cytotoxic agent.

TABLE II

Inhibition of Apomorphine-induced emesis in Beagles (0.1 mg/kg s.d.)

| Compounds | Dose (mg/kg s.c.) | No animals with emesis/tested | Emetic episodes ($\bar{X} \pm$ S.E.) | Latency time in min | No emetic episodes/ dog/2 hrs. |
|---|---|---|---|---|---|
| Saline | — | 12/12 | 6.7 ± 1.3 | 5 | 1,11,15,4,5,14,10,2,4,4,6,4. |
| FCE 23884 | 0.5000 | 0/2 | 0 | — | — |
| FCE 23884 | 0.1000 | 0/2 | 0 | — | — |
| FCE 23884 | 0.0500 | 0/2 | 0 | — | — |
| FCE 23884 | 0.0100 | 4/6 | 1.0 ± 0.4 | 9.5 | 0,1,3,0,1,1 |
| FCE 23884 | 0.0050 | 2/2 | 1.5 ± 0.5 | 7 | 2,1. |

TABLE III

Inhibition of Cisplatin-induced emesis in Beagles (3 mg/kg i.v.)

| Compounds | Dose (mg/kg i.v. × 2) | No animals with emesis/treated | Emetic episodes ($\bar{X} \pm$ S.E.) | Latency time in min | No emetic episodes/ dog/5 hrs.) |
|---|---|---|---|---|---|
| Saline | — | 11/11 | 9.4 ± 1.5 | 150 | 17,6,6,10,11,15,5,3,16, 8,6. |
| FCE 23884 | 0.2500 | 0/1 | 0 | — | — |
| FCE 23884 | 0.1250 | 1/4 | 0.25 ± 0.25 | 255 | 1,0,0,0. |
| FCE 23884 | 0.0625 | 3/4 | 5.5 ± 1.9 | 142 | 0,8,8,6. |
| METOCLOPRAMIDE | 6,0000 | 1/6 | 0.5 ± 0.5 | 270 | 0,0,3,0,0,0. |

Other compounds within formula (I) may be tested and found to be active in the above test.

We claim:

1. A method of treating emesis, which method comprises administering to a patient in need of said treatment a therapeutically effective amount of a compound of the formula I:

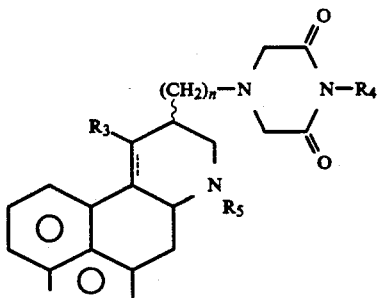

wherein n is 1 or 2, $R_1$ represents a hydrogen atom or a $C_1-C_4$ alkyl group, $R_3$ represents a hydrogen atom or a hydroxy group, the dash line represents optional ethylenic unsaturation, $R_4$ represents a hydrogen atom or a phenyl or $C_1-C_4$ alkyl group, $R_5$ represents a $C_1-C_4$ alkyl group or an allyl group and $R_6$ represents a hydrogen or halogen atom; or a pharmaceutically acceptable salt thereof.

2. A method according to claim 1, wherein the emesis has been induced by cancer therapy employing cisplatin.

3. A method according to claim 1, wherein $R_1$ is methyl.

4. A method according to claim 1, wherein $R_4$ is methyl.

5. A method according to claim 1, wherein $R_5$ is methyl.

6. A method according to claim 1, wherein the substituent in the 8-position is in the β-configuration.

7. A method according to claim 1, wherein $R_6$ is chlorine or bromine or hydrogen.

8. A method according to claim 1, in which the compound of formula I is 6-methyl-9,10-didehydro-8β-(3,5-dioxopiperazine-1-yl-methyl) ergoline.

* * * * *